United States Patent [19]
Hsueh et al.

[11] Patent Number: 5,336,215
[45] Date of Patent: Aug. 9, 1994

[54] EYE STABILIZING MECHANISM FOR USE IN OPHTHALMIC LASER SURGERY

[75] Inventors: Chi-Fu Hsueh, Escondido; Gregory J. Morris, La Jolla, both of Calif.; Stefan Goelz, Plankstadt, Fed. Rep. of Germany

[73] Assignee: Intelligent Surgical Lasers, San Diego, Calif.

[21] Appl. No.: 8,010

[22] Filed: Jan. 22, 1993

[51] Int. Cl.$^5$ .............................................. A61N 5/06
[52] U.S. Cl. ............................................ 606/4; 606/5;
606/6; 606/17; 606/10
[58] Field of Search ...................... 606/4, 5, 6, 107, 17, 606/10

[56] References Cited

U.S. PATENT DOCUMENTS

| | | | |
|---|---|---|---|
| 4,573,778 | 3/1986 | Shapiro | 606/4 X |
| 4,891,043 | 1/1990 | Zeimer et al. | 606/4 X |
| 4,903,695 | 2/1990 | Warner et al. | 606/4 |
| 4,905,711 | 3/1990 | Bennett et al. | 606/4 X |
| 4,994,058 | 2/1991 | Raven et al. | 606/5 |
| 5,013,311 | 5/1991 | Nouri | 606/4 |
| 5,108,412 | 4/1992 | Krumeich et al. | 606/4 X |
| 5,226,903 | 7/1993 | Mizuno | 606/4 X |

*Primary Examiner*—Peter A. Aschenbrenner
*Attorney, Agent, or Firm*—Nydegger & Associates

[57] ABSTRACT

An eye stabilizing mechanism for use with a computer controlled ophthalmic laser system includes a base on which the ophthalmic laser system is mounted. A frame is slidingly mounted on the base, and the frame is connected to the base by a linear spring. A contact lens is fixedly attached to the frame and an object lens is slidingly mounted on the frame. An object lens activating device is also fixedly attached to the frame, and this device is connected to the object lens to move the object lens in accordance with preprogrammed instructions from the computer. Thus, while contact is maintained between the surface of the eye and the contact lens, the object lens can be moved by computer control to move the focal point of the laser system through selected eye tissue. Also, any movement of the frame, due to movement of the eye, is opposed only by the substantially constant force which is established by the linear spring between the base and the frame.

21 Claims, 1 Drawing Sheet

EYE STABILIZING MECHANISM FOR USE IN OPHTHALMIC LASER SURGERY

FIELD OF THE INVENTION

The present invention pertains to devices which are useful for ophthalmic surgery. More particularly, the present invention is useful for stabilizing the eye of a patient during ophthalmic surgery wherein a laser system is used to alter selected tissue of the eye. The present invention is particularly, but not exclusively, useful for maintaining the eye of a patient in a predetermined position relative to the focal point of a laser beam, by physically constraining eye movement during ophthalmic laser surgery.

BACKGROUND OF THE INVENTION

Ophthalmic surgery is, unquestionably, one of the more complicated and difficult areas of medical practice. Though ophthalmic surgery is not normally a life threatening procedure, there is always the possibility of irreversible complications. Thus, ophthalmic surgery must be accomplished with great care and extreme precision.

In recent years, developments in laser systems have made new applications and new surgical procedures possible. One consequence of this is that ophthalmic surgery can be accomplished with greater surgical precision. Despite the advances in laser technology, the use of lasers for ophthalmic surgery still has certain operational limitations. Most importantly, it is absolutely essential that the laser be properly controlled during a surgical procedure. This requires that the proper position of the eye relative to the focal point of the laser be maintained at all times during the surgical procedure. Stated differently, the eye must remain stabilized in its relation to the laser system.

Although laser surgery can be accomplished relatively quickly, it still requires time. As a practical matter, movement of the laser's focal point must be accomplished with such extreme precision during a surgical operation that even the slightest movement of the eye can not be tolerated. Unfortunately, it is physically impossible for a patient to hold his/her eye sufficiently still for the length of time required to accomplish a surgical laser operation. Consequently, the eye must somehow be stabilized.

Essentially, there are two ways by which a patient's eye can be stabilized or held still relative to a laser system during an ophthalmic laser operation. One requires an optical link between the eye and the laser system, while the other requires a mechanical link. For an optical link, an optical arrangement which uses light reflections from the eye to generate signals that indicate eye movement is incorporated into the laser system. The laser system then uses these signals to compensate for eye movement. U.S. Pat. No. 4,848,340 which issued to Bille et al. for an invention entitled "Eyetracker and Method of Use", and which is assigned to the same assignee as the present invention, discloses such an optical arrangement. The second way is to mechanically stabilize the eye in its spacial relationship with the laser system through direct contact of the laser system's optical componentry with the eye. U.S. Pat. No. 4,712,543 which issued to Baron for an invention entitled "Process for Recurving the Cornea of an Eye" discloses such a system.

Regardless whether the eye stabilizing mechanism is an optical arrangement or a mechanical system, the mechanism must be compatible with the capabilities of the ophthalmic laser system with which it is used. In particular, the eye stabilizing mechanism must not limit the capabilities of the ophthalmic laser system. As can be easily appreciated, compatibility issues are even more pronounced when the laser system, as here, is computer controlled.

In light of the above, it is an object of the present invention to provide a mechanism which is useful for stabilizing an eye with a contact lens during ophthalmic laser surgery. It is another object of the present invention to provide an eye stabilizing mechanism which is incorporated directly into the optical system of a surgical laser generating device. Still another object of the present invention is to provide an eye stabilizing mechanism which establishes reliable contact between the laser system and the eye during ophthalmic laser surgery. Yet another object of the present invention is to provide an eye stabilizing mechanism which is operatively compatible with a computer controlled laser system. Another object of the present invention is to provide an eye stabilizing mechanism which does not cause injury or discomfort to the eye during surgery. It is also an object of the present invention to provide an eye stabilizing mechanism which is easy to use, relatively easy to manufacture and which is comparatively cost effective.

SUMMARY OF THE INVENTION

In accordance with the present invention, a device is disclosed which is useful with a laser system to mechanically stabilize the eye of a patient during ophthalmic laser surgery. The major components of this device include a base member, a frame member which is slidingly suspended on the base member, and a movable objective lens which is slidably mounted on the frame. Additionally, there is a contact lens that is fixedly mounted on the frame. This contact lens is contoured to conform to the surface of the eye for stabilizing engagement with the eye during surgery.

A compensating device, such as a linear force spring, connects the frame to the base member. Consequently, any sliding movement of the frame, and the objective lens along the base is opposed by the substantially constant force that is created by the spring. With this system, as the contact lens is initially positioned against the surface of the eye, a compensator force dependent on the substantially constant spring force is established between the contact lens and the eye. Thereafter, the force that is equivalent to the substantially constant spring force is maintained between the eye and the contact lens during any subsequent movement of the eye relative to the base.

As intended for the eye stabilizing mechanism of the present invention, a computer controlled laser system is provided which directs its laser beam through both the object lens and the contact lens. However, in order to control movement of the laser beam's focal point through selected eye tissue, the objective lens must be moveable relative to the contact lens. Consequently, an objective lens activating device, such as a galvo or a voice coil, is mounted directly on the frame and is connected to the objective lens to move the objective lens in accordance with preprogrammed instructions from the computer.

In addition to the substantially constant force which the mechanism of the present invention maintains between the surface of the eye and the contact lens, it can also include suction means for holding the contact lens against the surface of the eye. This additional feature can be established by forming channels in the frame which have openings near the periphery of the contact lens. A vacuum pump can then be connected in fluid communication with the channels via a flexible tube to establish a suction effect against the surface of the eye at the peripheral channel openings. When the eye's surface is in contact with the contact lens, this suction helps hold the eye against the contact lens.

In an alternate embodiment of the present invention, the frame can be fixedly mounted to the base with the contact lens slidably mounted on the frame. The stabilizing force between the contact lens and the surface of the eye can then be established by the weight of the contact lens and its support structure. For the alternate embodiment of the present invention, the mechanism also includes a first sensing means for locating the position of the contact lens relative to the frame, and a second sensing means for locating the position of the object lens relative to the frame. Again, the laser system is computer controlled. For the alternate embodiment, however, the computer uses signal from both the first and second sensing means to control movement of the object lens. Specifically, the movement of the object lens is controlled relative to the location of the contact lens for moving the laser system's focal point through eye tissue in accordance with preprogrammed instructions.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which.

DESCRIPTION OF THE PREFERRED EMBODIMENTS

Figure 1:
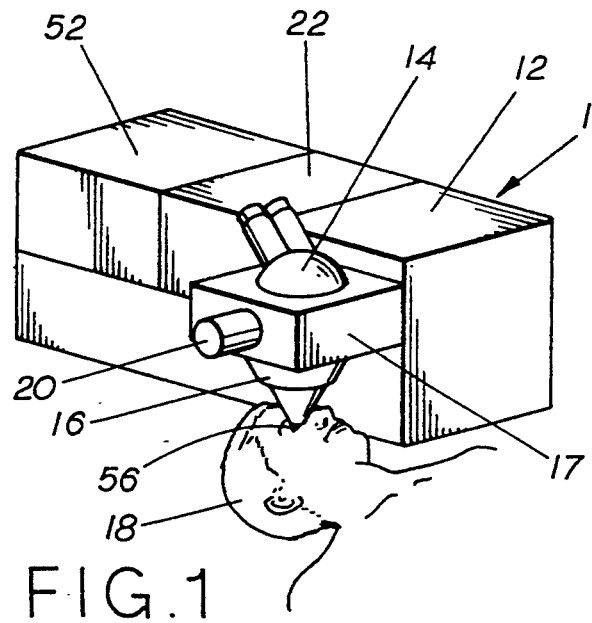
FIG. 1 is a perspective view of an ophthalmic surgical laser system which incorporates the eye stabilizing mechanism of the present invention, with the eyestabilizing mechanism in engagement with the eye of a patient.

Referring initially to FIG. 1, an ophthalmic laser system is shown and generally designated 10. For purposes of the present invention, the ophthalmic laser system 10 can be of any type well known in the pertinent art which uses a focused beam of laser energy to surgically alter the tissue of any eye. As shown, the laser system 10 includes a housing 12 on which a microscope 14 is mounted. The laser system 10 also includes an eye stabilizing mechanism, generally designated 16, which is mounted on a moveable platform 17 of the housing 12 for movement into contact with the eye of a patient 18 by operation of a motor 20.

Figure 2:
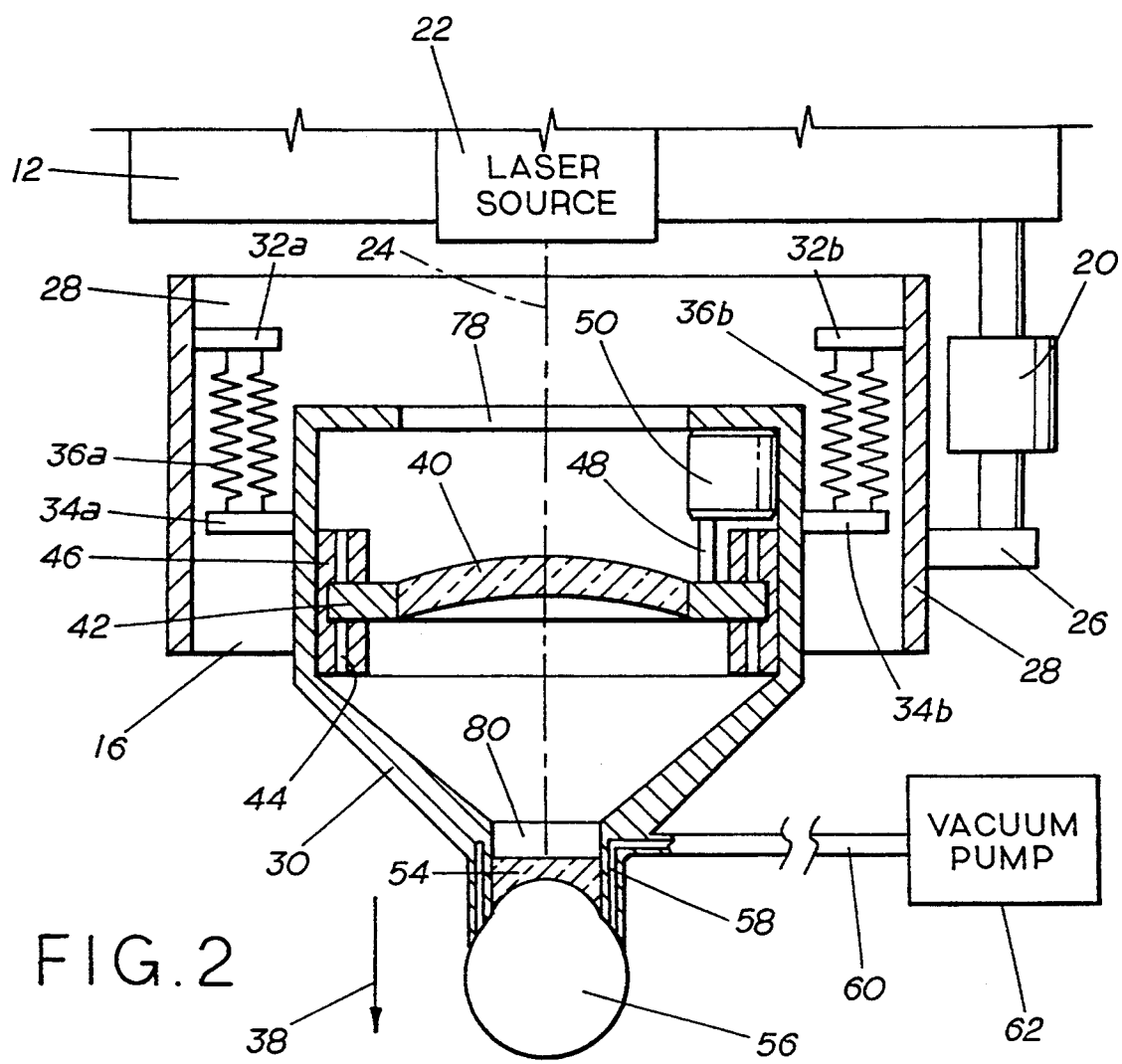
FIG. 2 is an elevational schematic drawing of the eye stabilizing mechanism of the present invention and its connections to the laser system, with portions shown in cross section for clarity.

Referring now to FIG. 2 it will be seen that a laser source 22 is mounted on the housing 12 of laser system 10. The laser source 22 can be of any type well known in the art which is capable of generating an ophthalmic laser beam 24. Furthermore, although the specific optical arrangement used to direct the laser beam 24 from laser source 22 to patient 18 through system 10 is not shown, it is to be appreciated that any known optical arrangement can be employed. The main concern is that the optical arrangement satisfy the needs of the operator and be compatible for use with the laser source 22 and the generated laser beam 24.

FIG. 2 shows that laser system 10 relies on a stable structural connection between the laser source 22 and eye stabilizing mechanism 16. For this purpose, it is shown that the laser source 22 is directly mounted on housing 12, and that the housing 12 includes a connector 26 which is fixedly attached to the base 28 of mechanism 16. As indicated above, however, it is necessary to be able to move and position the mechanism 16 in contact with the eye of patient 18 at the beginning of a surgical procedure. To do this, the activating motor 20 is provided between housing 12 and connector 26 which is part of platform 17 (not shown in FIG. 2). Motor 20 can be of any type which is well known in the pertinent art. And, although motor 20 can be activated to change the position of the entire mechanism 16 relative to housing 12, once an adjustment has been made with motor 20, the relationship between housing 12 and base 28 of mechanism 16 is fixed.

Still referring to FIG. 2 it is to be seen that eye stabilizing mechanism 16 includes a frame 30 which is suspended from the base 28. More specifically, an upper arm 32a,b is fixedly attached to the base 28 and a lower arm 34a,b is fixedly attached to the frame 30. A compensating device, such as a linear force spring 36a,b, interconnects the respective upper arm 32a,b to the lower arm 34a,b. Preferably, this compensating mechanism is a spring device, such as a constant force spring which generates a substantially constant force in opposition to any movement of the frame 30 relative to base 28 in the directions indicated by arrow 38. Through this compensating device, the frame 30 is suspended from base 28 and importantly, due to the linear force generated by springs 36a,b, any displacement of frame 30 from its equilibrium position will create a substantially constant opposing force. Preferably, this opposing force is in the approximate range of from zero to three hundred grams (0–300 gms). It is to be appreciated that means known in the art can be used to establish a desired value for this force according to the needs of the operator. In accordance with the present invention, a plurality of compensating mechanisms 36 can be employed.

An objective lens 40 is slidably mounted on the frame 30. More specifically, the lens 40 is held in a bracket 42 which has projections (not shown) that engage with the tracks 44 of a slide 46 that is mounted on the base 28. It is to be understood that there may be a plurality of slides 46, and that each slide 46 includes a pair of opposed tracks 44 which engage with the projections of a respective bracket 42 to allow a sliding movement of the frame 30 relative to the base 28. It is, of course, within the scope of the present invention to use any other type mechanism which is well known in the pertinent art and which allows the frame 30 to freely slide relative to the base 28.

The ophthalmic laser system 10 of the present invention also includes a link 48 which mechanically connects the objective lens 40 to an objective lens actuator 50. Importantly, the actuator 50 is mounted directly on the frame 30 for movement with the frame 30. Preferably, the objective lens actuator 50 is a GALVO, of a type well known in the pertinent art, but it can also be any other type actuator which is capable of sliding the objective lens along the frame 30 in a manner required for operation of the system 10, such as a voice coil.

Both the actuator 50 and the laser source 22 are electronically connected to a computer 52 which may be mounted in the housing 12 of laser system 10. With these electronic connections (not shown), actuator 50 is activated to move objective lens 40 back and forth on frame 30 in accordance with preprogrammed instructions from the computer 52 for the purpose of moving the focal point of laser beam 24 along a prescribed path for completion of the desired ophthalmic surgery.

FIG. 2 also shows that a contact lens 54 is mounted on frame 30 along the path of laser beam 24. This contact lens 54 is contoured to conform to the outer surface of the cornea of an eye 56 of the patient 18 and is made of any suitable material which is clear and which has minimal light dispersive properties. Additionally, it is shown that the frame 30 is formed with at least one channel 58 which has an open end near the periphery of the contact lens 54. A flexible tube 60 is provided which connects the channel 58, or all of the channels 58 if more than one channel 58 is used, with a vacuum pump 62. Consequently, upon engagement of the contact lens 54 with the cornea of eye 56, vacuum pump 62 can be operated to create a partial vacuum in the channel 58 which will assist in holding the eye 56 against the contact lens 54.

Figure 3:
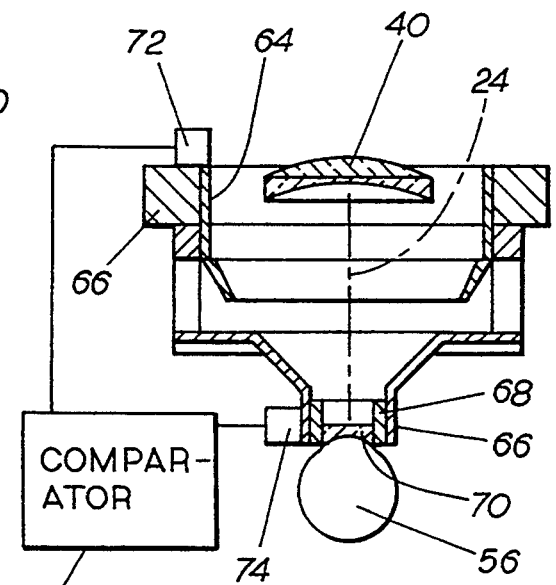
FIG. 3 is an elevational schematic drawing of an alternate embodiment of the eye stabilizing mechanism of the present invention with portions shown in cross section for clarity.

In an alternate embodiment of the present invention for an eye stabilizing mechanism, as shown in FIG. 3, an objective lens 40 is fixedly mounted on a bracket 64. The bracket 64, however, is slidably supported on a frame 66. Further, this embodiment of the present invention includes a support 68 which is also slidably supported on the frame 66. A contact lens 70 is then fixedly mounted on the support 68 for movement therewith relative to the frame 66. As for the preferred embodiment of the present invention, the contact lens 70 is contoured to conform to the outer surface of the cornea of the eye 56 of a patient 18. In accordance with the alternate embodiment of the present invention, however, the force which is generated to maintain contact between the eye 56 and the contact lens 70 is provided by the weight of the contact lens 70 and its support 68. Other mechanisms, of course, can be used. The important thing is that a substantially constant force be generated between the contact lens 70 and the eye 56. Again, this force is preferably in the approximate range of from ten to forty grams (10–40 gms).

Though not shown in FIG. 3, it is to be appreciated that a GALVO or some other appropriate activating mechanism, such as described above for the preferred embodiment, is used to move the bracket 64 and objective lens 40 relative to the frame 66. As shown in FIG. 3, the alternate embodiment of the present invention includes a sensor 72 which is mounted on frame 66 for the purpose of sensing movement between the objective lens 40 on bracket 64 and the frame 66. Similarly, a sensor 74 is mounted on frame 66 for the purpose of sensing movement between the contact lens 70 on support 68 and the frame 66.

A comparator 76 is electronically connected to both of the sensors 72 and 74 and, in accordance with preprogrammed instructions, the computer 76 uses signals from the sensors 72 and 74 to maintain the proper distance between objective lens 40 and contact lens 70 during an ophthalmic surgical operation. Though no actual electronic connections are shown, it is to be appreciated that the comparator 76 is part of the electronic system which is schematically shown in FIG. 1 and designated 52.

Operation

In the operation of the present invention, a patient 18 is positioned relative to the laser system 10 so that the operator can engage contact lens 54 with the eye 56 of patient 18. To do this, the operator, while viewing the patient's eye 56 through the eyepiece 14, manipulates the adjustment knob 20 to bring contact lens 54 of mechanism 16 into contact with the cornea of the eye 56. The compensating device 36 then establishes a substantially constant force between the eye 56 and the contact lens 54. If desired by the operator, the vacuum pump 62 can be activated to create a partial vacuum in the channels 58 to provide additional stability for the eye 56 during surgery. Any subsequent movement of the eye 56 will be opposed by the substantially constant force of the compensating device 36 and will cause movement of only the frame 30 and the components which are fixedly attached thereto.

As shown in FIG. 2 the frame 30 includes an opening 78 and an aperture 80 which establish an unobstructed path for laser beam 24 from the laser source 22, through both objective lens 40 and contact lens 54, and into the eye 56. In accordance with the structure disclosed for the preferred embodiment of the present invention, the eye 56 is maintained in a fixed relationship with the frame 30. Consequently, movement of objective lens 40 on frame 30 by activation of the objective lens actuator 50 results in the movement of the focal point of laser beam 24. This movement, when accomplished according to preprogrammed instructions from the computer 52, can be controlled to move the focal point of laser beam 24 along a prescribed path in the tissue of eye 56. Depending on the particular laser used, the energy level of the laser, its spot size, and the path which is established for movement of the focal point of the laser, ophthalmic surgery can be accomplished as desired by the operator while the mechanism 16 of the present invention stabilizes the eye 56 relative to the laser.

While the particular eye stabilizing mechanism for the present invention as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. A mechanism for stabilizing an eye with a contact lens and compensating for eye movement relative to the focal point of a laser beam during ophthalmic laser surgery which comprises:

a base;

means for supporting a contact lens, said supporting means being slidably mounted on said base;

means, attached to said base and connected to said supporting means, for generating a force against said supporting means to hold said contact lens against the eye; and means mounted on said supporting means for moving said focal point along a preselected path relative to said contact lens to perform said surgery.

2. A mechanism as recited in claim 1 wherein said supporting means is a frame and said contact lens is slidably mounted on said frame for resting against the eye.

3. A mechanism as recited in claim 2 wherein said force generating means is a weight attached to said contact lens.

4. A mechanism as recited in claim 2 wherein said moving means is an objective lens slidably mounted on said frame for movement of said focal point, and said mechanism further comprises first means for locating said contact lens relative to said frame and second means for locating said objective lens relative to said frame.

5. A mechanism as recited in claim 1 wherein said supporting means is a frame and said contact lens is fixedly mounted on said frame.

6. A mechanism as recited in claim 5 wherein said force generating means connects said frame to said base for maintaining a substantially constant force between said contact lens and the eye.

7. A mechanism as recited in claim 6 wherein said substantially constant force is in the approximate range of between zero and three hundred grams (0–300 gms).

8. A mechanism as recited in claim 6 wherein said frame is formed with an open channel having a first end and a second end, said second end of said channel being positioned against the eye when said contact lens is in contact with the eye, and wherein said mechanism further comprises:
   a device selectively operable for creating a partial vacuum; and
   a tube connecting said vacuum creating device with said first end of said channel to establish a partial vacuum at said second end of said channel to hold the eye against said contact lens.

9. A mechanism as recited in claim 1 wherein said moving means comprises:
   a computer mounted on said base;
   an objective lens slidably mounted on said supporting means;
   a computer controlled objective lens actuator fixedly mounted on said supporting means and electronically connected to said computer; and
   a link connecting said objective lens actuator with said objective lens for movement of said objective lens on said supporting means in accordance with preprogrammed instructions from said computer.

10. A support apparatus for holding a contact lens against the cornea of an eye during ophthalmic surgery involving movement of a focal point of a laser system which comprises:
    a base;
    a frame for holding a contact lens, said frame being slidably mounted on said base;
    a compensating device connecting said frame to said base for maintaining a substantially constant force between said contact lens and the cornea of the eye;
    an objective lens slidably mounted on said frame; and
    means, mounted on said apparatus, for moving said objective lens relative to said contact lens to selectively move said focal point of said laser system.

11. An apparatus as recited in claim 10 wherein said moving means comprises:
    a computer mounted on said base;
    a computer controlled objective lens actuator fixedly mounted on said frame and electronically connected to said computer; and
    a link connecting said objective lens actuator with said objective lens for movement of said objective lens on said frame in accordance with preprogrammed instructions from said computer.

12. An apparatus as recited in claim 10 wherein said substantially constant force is in the approximate range of between zero and three hundred grams (0–300 gms).

13. An apparatus as recited in claim 10 wherein said compensating device is a spring.

14. An apparatus as recited in claim 10 further comprising suction means for holding said contact lens in engagement with the cornea of the eye.

15. An apparatus as recited in claim 14 wherein said frame is formed with an open channel having a first end and a second end, said second end of said channel being positioned in contact with the cornea of the eye when said contact lens is in contact with the cornea of the eye, and wherein said suction means comprises:
    a device selectively operable for creating a partial vacuum; and
    a tube connecting said vacuum creating device with said first end of said channel to establish a partial vacuum at said second end of said channel to hold the cornea of the eye against said contact lens.

16. A method for stabilizing the eye of a patient during ophthalmic laser surgery using an apparatus comprising a base, means slidably mounted on said base for supporting a contact lens, means mounted on said base and connected to said supporting means for generating a force against the supporting means to hold the contact lens against the eye, and means mounted on said supporting means for moving the focal point of a laser system along a preselected path relative to said contact lens; the method comprising the steps of:
    positioning the contact lens against the eye;
    locating the objective lens of the laser system relative to the contact lens to establish a predetermined starting position for the focal point of the laser system; and
    maneuvering the focal point of the laser system along the preselected path to perform the ophthalmic surgery.

17. A method as recited in claim 16 wherein the supporting means is a frame and the frame is formed with an open channel having a first end and a second end, the second end of the channel being positioned against the eye when the contact lens is in contact with the eye, and wherein the apparatus further includes a device selectively operable for creating a partial vacuum; and the method further comprises the step of connecting a tube between the vacuum creating device and the first end of the channel to establish a partial vacuum at the second end of the channel to hold the eye against the contact lens.

18. A method as recited in claim 17 further comprising the step of generating a substantially constant force between the contact lens and the eye wherein the substantially constant force is in the approximate range of between zero and three hundred grams (0–300 gms).

19. A method as recited in claim 16 wherein the focal point is maneuvered along a preselected path for intrastromal photoablation.

20. A method as recited in claim 16 wherein the focal point is maneuvered along a preselected path for a phacoemulsification procedure.

21. A mechanism for stabilizing eye movement relative to the focal point of a laser beam during ophthalmic laser surgery which comprises:
   a base;
   a frame slidably mounted on said base and formed with an open channel having a first end and a second end, said second end of said channel being positionable against the eye;
   means, mounted on said base and connected to said frame, for generating a force against said frame to hold said second end of said channel against the eye;
   a device selectively operable for creating a partial vacuum;
   a tube connecting said vacuum creating device with said first end of said channel to establish a partial vacuum at said second end of said channel to hold the eye against said frame: and
   means mounted on said frame for moving said focal point along a preselected path relative to said frame to perform said surgery.

* * * * *